United States Patent
Dyckman et al.

(10) Patent No.: US 7,314,876 B2
(45) Date of Patent: *Jan. 1, 2008

(54) ARYL KETONE PYRROLO-TRIAZINE COMPOUNDS USEFUL AS KINASE INHIBITORS

(75) Inventors: Alaric J. Dyckman, Lawrenceville, NJ (US); Katerina Leftheris, Skillman, NJ (US); John Hynes, Washington Crossing, PA (US); Arthur M P. Doweyko, Long Valley, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/420,445

(22) Filed: Apr. 22, 2003

(65) Prior Publication Data

US 2003/0232831 A1    Dec. 18, 2003

Related U.S. Application Data

(60) Provisional application No. 60/374,907, filed on Apr. 23, 2002.

(51) Int. Cl.
| | | |
|---|---|---|
| C07D 487/04 | (2006.01) | |
| C07D 471/04 | (2006.01) | |
| A61K 31/53 | (2006.01) | |
| A61K 31/4427 | (2006.01) | |
| A61P 9/10 | (2006.01) | |
| A61P 19/02 | (2006.01) | |
| A61P 19/08 | (2006.01) | |
| A61P 1/00 | (2006.01) | |

(52) U.S. Cl. ...................... 514/243; 544/183
(58) Field of Classification Search ............... 544/183; 514/243

See application file for complete search history.

(56) References Cited

U.S. PATENT DOCUMENTS

| 6,147,080 | A | 11/2000 | Bemis et al. |
|---|---|---|---|
| 6,251,914 | B1 | 6/2001 | Adams et al. |
| 6,277,989 | B1 | 8/2001 | Chakravarty et al. |
| 6,670,357 | B2 * | 12/2003 | Leftheris et al. ............ 514/218 |
| 2002/0065270 | A1 | 5/2002 | Moriarty et al. |
| 2002/0137747 | A1 | 9/2002 | Moriarty et al. |
| 2003/0069244 | A1 | 4/2003 | Leftheris et al. |
| 2003/0139435 | A1 | 7/2003 | Ahmed et al. |
| 2003/0186982 | A1 | 10/2003 | Godfrey, Jr. et al. |
| 2003/0186983 | A1 | 10/2003 | Mastalerz et al. |
| 2004/0023992 | A1 | 2/2004 | Das et al. |
| 2004/0063707 | A1 | 4/2004 | Bhide et al. |
| 2004/0063708 | A1 | 4/2004 | Bhide et al. |
| 2004/0072832 | A1 | 4/2004 | Bhide et al. |
| 2004/0077858 | A1 | 4/2004 | Bhide et al. |
| 2004/0142931 | A1 | 7/2004 | Vite et al. |

FOREIGN PATENT DOCUMENTS

| WO | WO00/20402 | 4/2000 |
|---|---|---|
| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |
| WO | WO 02/40486 | 5/2002 |
| WO | WO 03/091229 | 11/2003 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, p. 596.*
Henry et al., Drugs. Fut., vol. 24, pp. 1345-1354 (1999).
Rankin et al., Br. J. Rheumatol., vol. 34, pp. 334-342 (1995).
Moreland et al., Ann. Intern.Med., vol. 130, pp. 478-486 (1999).
Branger, J., et al., "Anti-Inflammatory Effects of a p38 Mitogen-Activated Protein Kinase Inhibitor During Human Endotoxemia", The Journal of Immunology, vol. 168, pp. 4070-4077, (2002).
Davis, J. C., Jr., "Understanding the Role of Tumor Necrosis Factor Inhibition in Ankylosing Spondylitis", Seminars in Arthritis and Rheumatism, vol. 34, pp. 668-677, (2004).
Gottlieb, A. B., et al., TNF Inhibition Rapidly Down-Regulates Multiple Proinflammatory Pathways in Psoriasis Plaques[1], The Journal of Immunology, vol. 175, pp. 2721-2729, (2005).
Hideshima, T. et al, "Targeting p38 MAPK inhibits multiple myeloma cell growth in the bone marrow milieu", Blood, vol. 101(2), pp. 703-706, (2003).

(Continued)

Primary Examiner—Venkataraman Balasubramanian
(74) Attorney, Agent, or Firm—Anastasia P. Winslow; Joseph C. Wang

(57) ABSTRACT

Compounds having the formula (I), and pharmaceutically acceptable salts, prodrugs, and solvates thereof, are surprisingly advantageous as p38 kinase inhibitors, wherein $R_3$ is hydrogen, methyl, perfluoromethyl, methoxy, halogen, cyano, $NH_2$, or $NH(CH_3)$, preferably methyl; X is N or CH; and $R_1$ through $R_6$ are as described in the specification.

3 Claims, No Drawings

OTHER PUBLICATIONS

Johansen, C., et al., "Protein Expression of TNF-α in Psoriatic Skin Is Regulated at a Posttranscriptional Level by MAPK-Activated Protein Kinase 2[1]", The Journal of Immunology, vol. 176, pp. 1431-1438, (2006).

Johansen, C., et al., "The mitogen-activated protein kinases p38 and KRK1/2 are increased in lesional psoriatic skin", British Journal of Dermatology, vol. 152, pp. 37-42, (2005).

Kumar, S., et al., "P38 MAP Kinases: Key Signalling Molecules as Therapeutic Targets for Inflammatory Diseases", vol. 2, pp. 717-726, (2003).

Mease, P. J., et al., "Psoriatic arthritis treatment: biological response modifiers", Ann. Rheum. Dis., vol. 64 (Suppl. II), pp. ii78-ii82, (2005).

Navas, TA, et al., Inhibition of p38α MAPK enhances proteasome inhibitor-induced apoptosis of myeloma cells by modulating Hsp27, Bcl-$X_L$, MCl-1 and p53 levels in vitro and inhibits tumor growth in vivo, Leukemia, 1-11 (2006).

Papp. K. A., "The long-term efficacy and safety of new biological therapies for psoriasis", Arch. Dermatol. Res. vol. 298, pp. 7-15, (2006).

Saklatvala, J., "The p38 MAP kinase pathway as a therapeutic target in inflammatory disease", Current Opinion in Pharmacology, vol. 4, pp. 372-377, (2004).

Waetzig G. H., "p38 Mitogen-Activated Protein Kinase Is Activated and Linked to TNF-α Signaling in Inflammatory Bowel Disease[1]", The Journal of Immunology, vol. 168, pp. 5342-5351, (2002).

* cited by examiner

ARYL KETONE PYRROLO-TRIAZINE COMPOUNDS USEFUL AS KINASE INHIBITORS

This application claims priority to U.S. Provisional Application No. 60/374,907 filed Apr. 23, 2002; the entirety of which is incorporated herein by reference.

FIELD OF THE INVENTION

This invention relates to pyrrolotriazine compounds, more particularly, to aryl and heteroaryl ketone pyrrolo-triazine compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α; and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to SmithKline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain pyrrolotriazine compounds, particularly, aryl and heteroaryl ketone pyrrolotriazine aniline compounds useful as kinase inhibitors, particularly kinases p38α and β. Pyrrolotriazine compounds useful as tyrosine kinase inhibitors are disclosed in U.S. patent application Ser. No. 09/573,829, filed May 18, 2000, assigned to the present assignee. Methods of treating p38 kinase-associated conditions as well as pyrrolotriazine carboxamide and benzamide compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001. Pyrrolotriazine compounds substituted with an acidic group reportedly having sPLA₂-inhibitory activity are disclosed in WO 01/14378 A1 to Shionogi & Co., Ltd, published Mar. 1, 2001 in Japanese. Each of the patent applications, patents, and publications referred to herein is incorporated herein by reference.

SUMMARY OF THE INVENTION

The instant invention pertains to compounds of formula (I), which are surprisingly advantageous as inhibitors of kinases p38α and β,

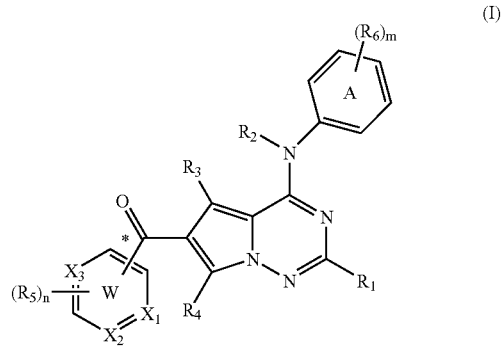

(I)

and pharmaceutically-acceptable salts, prodrugs, and solvates thereof, wherein:

$X_1$, $X_2$ and $X_3$ are independently selected from N and CH, wherein when $X_1$, $X_2$ and/or $X_3$ is CH, the hydrogen atom of said $X_1$, $X_2$ and/or $X_3$ is optionally replaced with a substituent $R_5$ or a bond joining ring W to C*;

$R_1$ and $R_4$ are independently selected from hydrogen, alkyl, substituted alkyl, —OR$_8$, —SR$_8$, —OC(=O)R$_8$, —CO$_2$R$_8$, —C(=O)NR$_8$R$_9$, —NR$_8$R$_9$, —S(=O)R$_8$, —SO$_2$R$_8$, —SO$_2$NR$_8$R$_9$, —NR$_{10}$SO$_2$NR$_8$R$_9$, —NR$_{10}$SO$_2$R$_8$, —NR$_8$C(=O)R$_9$, —NR$_8$CO$_2$R$_9$, —NR$_{10}$C(=O)NR$_8$R$_9$, halogen, nitro, and cyano;

$R_2$ is hydrogen or $C_{1-4}$alkyl;

$R_3$ is hydrogen, methyl, perfluoromethyl, methoxy, halogen, cyano, NH$_2$, or NH(CH$_3$);

$R_5$ is attached to any available carbon atom of the aryl or heteroaryl ring W and at each occurrence is independently selected from alkyl, halogen, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkylsulfonyl, sulfonamido, phenyl, benzyl, aryloxy, and benzyloxy, and/or two of the $R_5$ groups may be taken together to form a five or six membered fused carbocyclic, heterocyclic, or heteroaryl ring, wherein each $R_5$ group and/or each fused ring formed by two $R_5$ groups in turn optionally may be substituted with up to two $R_{11}$;

$R_6$ is attached to any available carbon atom of the phenyl ring A and at each occurrence is independently selected from alkyl, halogen, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkylsulfonyl, sulfonamido, phenyl, benzyl, aryloxy, and benzyloxy, wherein each $R_6$ group in turn optionally may be substituted by up to two $R_{12}$;

$R_8$, $R_9$ and $R_{10}$ are independently selected from hydrogen, alkyl, substituted alkyl, aryl, heteroaryl, cycloalkyl and heterocyclo;

$R_{11}$ and $R_{12}$ are independently selected from hydroxy, alkyl, substituted alkyl, alkoxy, aryl, aralkyl, and aryl substituted with zero to three of $C_{1-4}$alkyl, $C_{2-6}$alkenyl, halogen, trifluoromethyl, trifluoromethoxy, cyano, nitro, amino, $C_{1-4}$alkylamino, amino$C_{1-4}$alkyl, hydroxy, hydroxy$C_{1-4}$alkyl, alkoxy, and $C_{1-4}$alkylthio; and m and n are 0, 1, 2 or 3.

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The term "substituted alkyl" refers to an alkyl group substituted by one to four substituents selected from halogen, hydroxy, alkoxy, keto (═O), alkanoyl, aryloxy, alkanoyloxy, $NR_aR_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —SO$_2$NR$_a$R$_b$, nitro, cyano, —CO$_2$H, —CONR$_a$R$_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for substituted alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups. Each ring of the aryl may be optionally substituted with one to three $R_c$ groups, wherein $R_c$ at each occurrence is selected from alkyl, substituted alkyl, halogen, trifluoromethoxy, trifluoromethyl, —SR, —OR, —NRR', —NRSO$_2$R', —SO$_2$R, —SO$_2$NRR', —CO$_2$R', —C(═O)R', —C(═O)NRR', —OC(═O)R', —OC(═O)NRR', —NRC(═O)R', —NRCO$_2$R', phenyl, $C_{3-7}$cycloalkyl, and five-to-six membered heterocyclo or heteroaryl, wherein each R and R' is selected from hydrogen, alkyl, substituted alkyl, alkenyl, substituted alkenyl, phenyl, $C_{3-7}$cycloalkyl, and five-to-six membered heterocyclo or heteroaryl, except in the case of a sulfonyl group, then R is not going to be hydrogen. Each substituent $R_c$ optionally in turn may be further substituted by one or more (preferably 0 to 2) $R_d$ groups, wherein $R_d$ is selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group

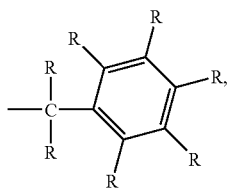

wherein each R group may be hydrogen or may also be selected from $R_c$ as defined above, in turn optionally substituted with one or more $R_d$. At least two of these "R" groups should be hydrogen and preferably at least five of the "R" groups is hydrogen. A preferred benzyl group involves the alkyl-portion being branched to define

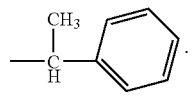

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted with one to three (preferably 0 to 2) $R_c$ groups, as defined above for aryl, which in turn may be substituted with one or more (preferably o to 2) $R_d$ groups, also as recited above.

Exemplary monocyclic heteroaryl groups include pyrrolyl, pyrazolyl, pyrazolinyl, imidazolyl, oxazolyl, isoxazolyl, thiazolyl (i.e.,

thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a $C_3$-$C_7$ carbocylic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from $R_c$ groups, as recited above, and/or from keto (where appropriate) which in turn may be substituted with one to three $R_d$ groups, also as recited above. Thus, when it is stated that a carbon-carbon bridge may be optionally substituted, it is meant that the carbon atoms in the bridged ring optionally may be substituted with an $R_c$ group, which preferably is seleted from $C_{1-4}$alkyl, $C_{2-4}$alkenyl, halogen, haloalkyl, haloalkoxy, cyano, amino, $C_{1-4}$alkylamino, amino$C_{1-4}$alkyl, hydroxy, hydroxy$C_{1-4}$alkyl, and $C_{1-4}$alkoxy. Exemplary groups include cyclopropyl, cyclobutyl, cyclopentyl, cyclohexyl, cycloheptyl, bicycloheptane, cyclooctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (=O), and/or one or more $R_c$ groups, as recited above, which in turn may be substituted with one to three $R_d$ groups, also as recited above.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., indolyl), the reference is intended to include rings having 0 to 3, preferably 0-2, substituents selected from those recited above for the the aryl, cycloalkyl, heterocyclo and/or heteroaryl groups, as appropriate. Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of formula (I), when a substituent is a cyclopropyl ring, preferably the ring has no more than two substituents, and preferably said substituents do not comprise nitro ($NO_2$), more than one cyano group, or three halogen groups. Similarly, when m is 3, preferably $R_6$, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkoxy is —$OR^e$, alkanoyl is —$C(=O)R^e$, aryloxy is —OAr, alkanoyloxy is —$OC(=O)R^e$, amino is —$NH_2$, alkylamino is —$NHR^e$ or —$N(R^e)_2$, arylamino is —NHAr or —$NR^eAr$, aralkylamino is —NH—$R^f$—Ar, alkanoylamino is —NH—$C(=O)R^e$, aroylamino is —NH—$C(=O)Ar$, aralkanoylamino is —NH—$C(=O)R^f$—Ar, thiol is —SH, alkylthio is —$SR^e$, arylthio is —SAr, aralkylthio is —S—$R^f$—Ar, alkylthiono is —$S(=O)R^e$, arylthiono is —$S(=O)Ar$, aralkylthiono is —$S(=O)R^f$—Ar, alkylsulfonyl is —$SO_{(q)}R^e$, arylsulfonyl is —$SO_{(q)}Ar$, arylsulfonylamine is —$NHSO_{(q)}Ar$, alkylsulfonylamine is —$NHSO_2R^e$, aralkylsulfonyl is —$SO_{(q)}R^fAr$, sulfonamido is —$SO_2NH_2$, substituted sulfonamide is —$SO_2NHR^e$ or —$SO_2N(R^e)_2$, nitro is —$NO_2$, carboxy is —$CO_2H$, carbamyl is —$CONH_2$, substituted carbamyl is —$C(=O)NHR^g$ or —$C(=O)NR^gR^h$, alkoxycarbonyl is —$C(=O)OR^e$, carboxyalkyl is —$R^f$—$CO_2H$, sulfonic acid is —$SO_3H$, arylsulfonylamine is —$NHSO_{(q)}Ar$, guanidino is

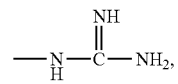

and ureido is

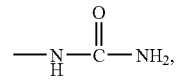

wherein $R^e$ is alkyl or substituted alkyl as defined above, $R^f$ is alkylene or substituted alkylene as defined above, $R^g$ and $R^h$ are selected from alkyl, substituted alkyl, aryl, aralkyl, cycloalkyl, heterocyclo, and hetearyl; Ar is an aryl as defined above, and q is 2 or 3.

Throughout the specification, groups and substituents thereof may be chosen by one skilled in the field to provide stable moieties and compounds.

The compounds of Formula (I) may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the Formula (I) may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred compounds are those having the formula (Ia),

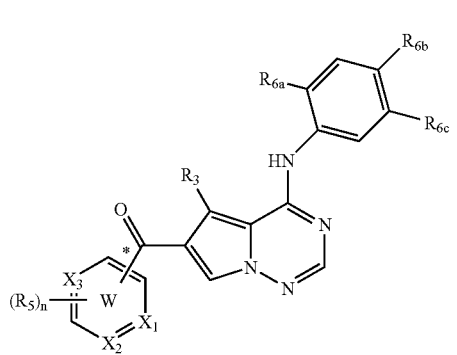

(Ia)

and pharmaceutically-acceptable salts, prodrugs, and solvates thereof, wherein:

$X_1$, $X_2$ and $X_3$ are independently selected from N and CH, wherein when $X_1$, $X_2$ and/or $X_3$ is CH, the hydrogen atom of said $X_1$, $X_2$ and/or $X_3$ group is optionally replaced with a substituent $R_5$ or a bond joining ring W to C*;

$R_3$ is methyl, —$CF_3$, or —$OCF_3$;

$R_5$ is lower alkyl, substituted $C_{1-4}$alkyl, halogen, trifluoromethoxy, trifluoromethyl, hydroxy, or —O($C_{1-4}$alkyl);

$R_{6a}$ and $R_{6b}$ are independently selected from hydrogen, $C_{1-6}$alkyl, substituted $C_{1-4}$alkyl, halogen, trifluoromethoxy, trifluoromethyl, —$OR_{13}$, —C(=O)alkyl, —OC(=O)alkyl, —$NR_{13}R_{14}$, —$SR_{13}$, —$NO_2$, —CN, —$CO_2R_{13}$, —$CONH_2$, —$SO_3H$, —S(=O)alkyl, —S(=O)aryl, —$NHSO_2$-aryl-$R_{13}$, —$SO_2NHR_{13}$, —$CONHR_{13}$, and —NHC(=O)$NHR_{13}$;

$R_{6c}$ is selected from hydrogen, alkyl, hydroxyalkyl, alkoxyalkyl, carboxy, carboxyalkyl, alkoxycarbonyl, carbamyl, ureido, alkanoylamino, aroylamino, and aralkanoylamino, wherein each $R_{6c}$ in turn is optionally substituted with one to two groups selected from alkyl, hydroxy, alkoxy, hydroxyalkyl, and alkoxyalkyl; and $R_{13}$ and $R_{14}$ are selected from hydrogen, $C_{1-4}$alkyl, phenyl, $C_{3-7}$cycloalkyl, and five-to-six membered heterocyclo and heteroaryl; and n is 1, 2 or 3.

More preferably, in compounds of formula (Ia), above, $R_{6a}$ and $R_{6b}$ are independently selected from hydrogen, $C_{1-4}$alkyl, substituted $C_{1-4}$alkyl, halogen, trifluoromethoxy, trifluoromethyl, hydroxy, and —O($C_{1-4}$alkyl); and $R_{6c}$ is selected from hydrogen, $C_{1-6}$alkyl, —$CO_2CH_3$, —NHC(=O)$R_7$, and —C(=O)$NHR_7$, wherein $R_7$ is hydrogen, alkyl, alkoxy, or hydroxyalkyl.

In compounds of formula (I), preferably $R_1$ and $R_4$ are hydrogen or $CH_3$.

In compounds of formula (I), preferably $R_2$ is hydrogen.

In compounds of formula (I), preferably $R_3$ is methyl, —$CF_3$, or —$OCF_3$.

In compounds of formula (I), preferably $R_5$ is lower alkyl, substituted $C_{1-4}$alkyl, halogen, trifluoromethoxy, trifluoromethyl, hydroxy, or —O($C_{1-4}$alkyl), and n is 1, 2 or 3.

Also preferred are compounds, having the formula (Ib),

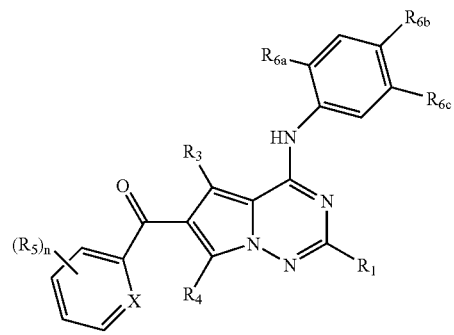

(Ib)

and pharmaceutically-acceptable salts, prodrugs, and solvates thereof, wherein

X is N or CH;

$R_1$ and $R_4$ are independently hydrogen, halogen, or $CH_3$;

$R_3$ is methyl, —$CF_3$, or —$OCF_3$;

$R_5$ is $C_{1-4}$alkyl, $C_{2-6}$alkenyl, halogen, trifluoromethyl, trifluoromethoxy, cyano, nitro, amino, $C_{1-4}$alkylamino, amino$C_{1-4}$alkyl, hydroxy, hydroxy$C_{1-4}$alkyl, alkoxy, alkoxy$C_{1-4}$alkyl, and $C_{1-4}$alkylthio;

$R_{6a}$ and $R_{6b}$ are selected from hydrogen, $C_{1-4}$alkyl, substituted $C_{1-4}$alkyl, halogen, trifluoromethoxy, trifluoromethyl, hydroxy, and —O($C_{1-4}$alkyl);

$R_{6c}$ is selected from hydrogen, alkyl, hydroxyalkyl, alkoxyalkyl, carboxy, carboxyalkyl, alkoxycarbonyl, carbamyl, ureido, alkanoylamino, aroylamino, and aralkanoylamino, wherein each $R_{6c}$ in turn is optionally substituted with one to two groups selected from alkyl, hydroxy, alkoxy, hydroxyalkyl, and alkoxyalkyl; and n is 1, 2 or 3.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally.

Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown surprisingly advantageous activity as inhibitors of p38α/β enzymes and TNF-α. In particular, compounds of formula (I), exemplified herein, have demonstrated activity in inhibiting the p38α/β enzymes with $IC_{50}$ values (concentration required to inhibit 50% of specific binding) below 500 nM.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; [γ-$^{33}$P]ATP, 3 nM,; MBP (Sigma, #M1891), 2 μg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
Pd=palladium
Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point HPLC Conditions: YMC S5 ODS 4.6×50 mm Ballistic column, 4 mL/min flow rate, 4 min. linear gradient elution (Start solvent % B=0; Final solvent % B=100), solvent A=10% MeOH/90% $H_2O$/0.2% $H_3PO_4$. Solvent B=90% MeOH/10% $H_2O$/0.2% $H_3PO_4$ Methods of Preparation Compounds of formula I may generally be prepared according to the following schemes and the knowledge of one skilled in the art, and/or the methods described in U.S. patent application Ser. Nos. 10/036,293 and/or 09/573,829, incorporated herein by reference. In the schemes, the groups $R_1$-$R_6$, X, m and n are as described herein for compounds of Formula (I), and Ar denotes the aryl or heteroaryl ring W.

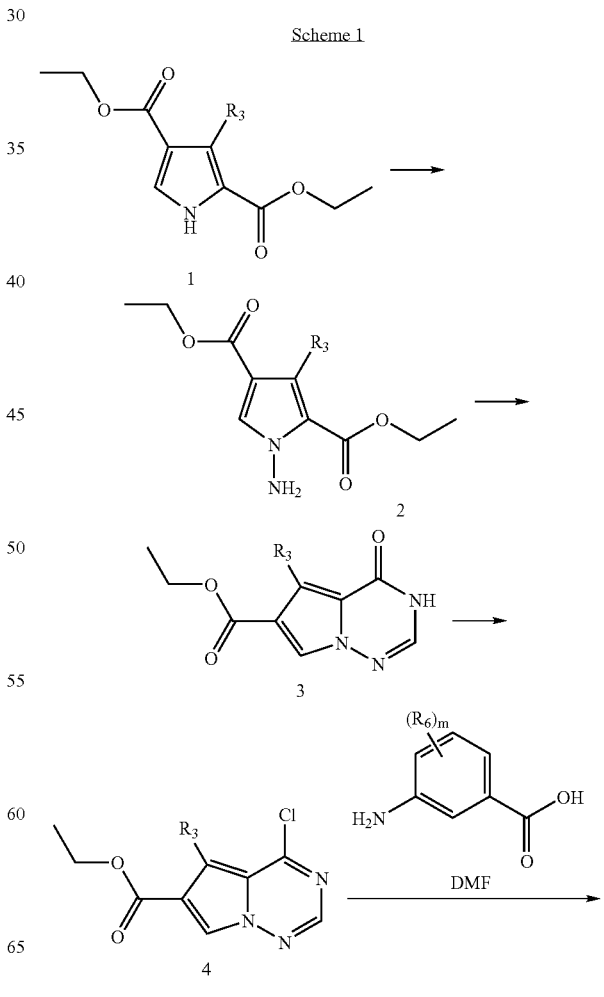

-continued

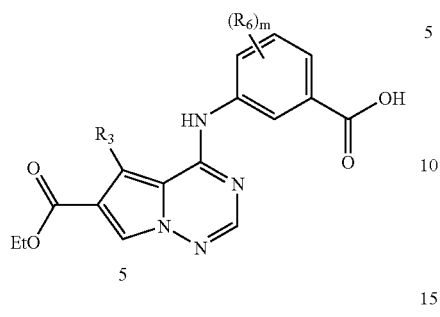

3-methyl-1-pyyrole-2,4-diethyl ester can be reacted with chloramine in ether to produce compound (2). Reacting compound (2) in formamide with acetic acid produces compound (3). Compound (3) can be reacted with DIPEA and POCl₃ in toluene to produce compound (4). Compound (4) can be reacted with an appropriate amino benzoic acid in DMF to afford compound (5).

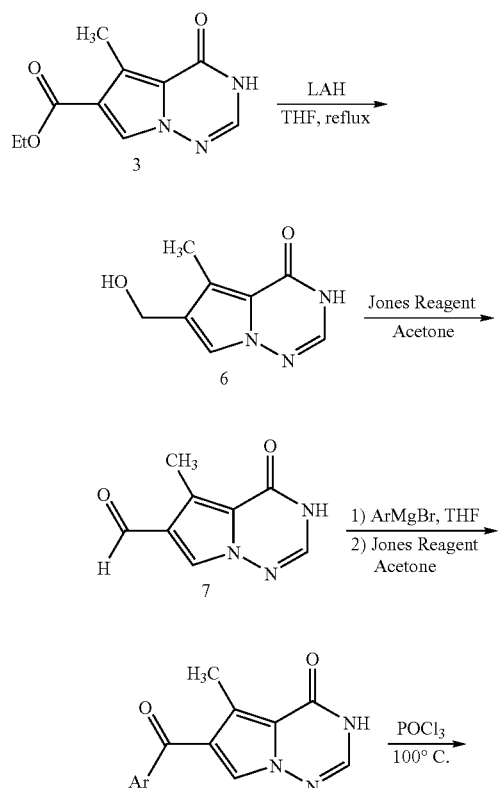

-continued

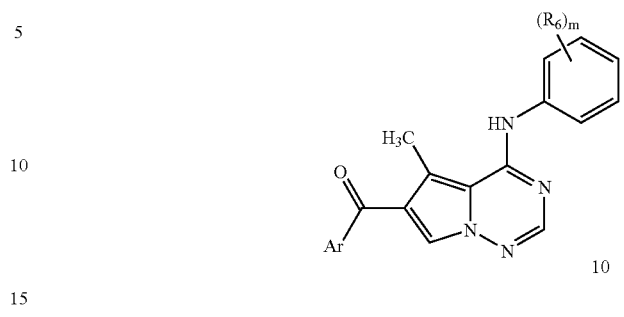

Reduction of the ester group of pyrrolotriazine 3 (see Scheme 1) with a suitable reducing agent such as LAH in an aprotic organic solvent such as THF produces the alcohol (6). Alcohol (6) is oxidized to the aldehyde (7) with a suitable oxidant, such as Jones Reagent. Aldehyde (7) is reacted with a suitable organometallic reagent (such as phenylmagnesium bromide) to afford an intermediate secondary alcohol product that is subsequently oxidized to ketone (8) with a suitable oxidant, such as Jones Reagent. A chlorinating agent, such as POCl₃, is used to convert (8) to chloride (9). Chloride (9) is reacted with an aniline in a suitable solvent, such as DMF, at rt or elevated temperature to provide product (10), a compound of formula (I).

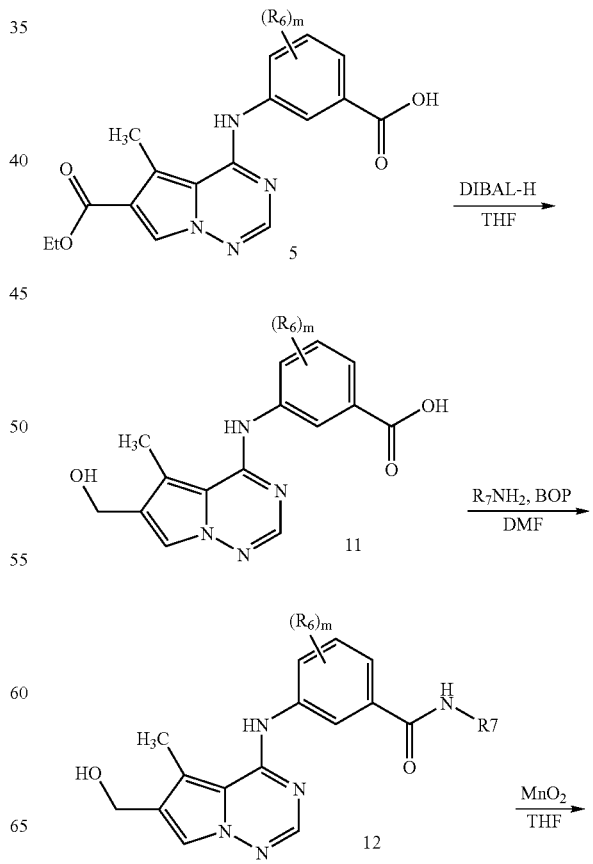

-continued

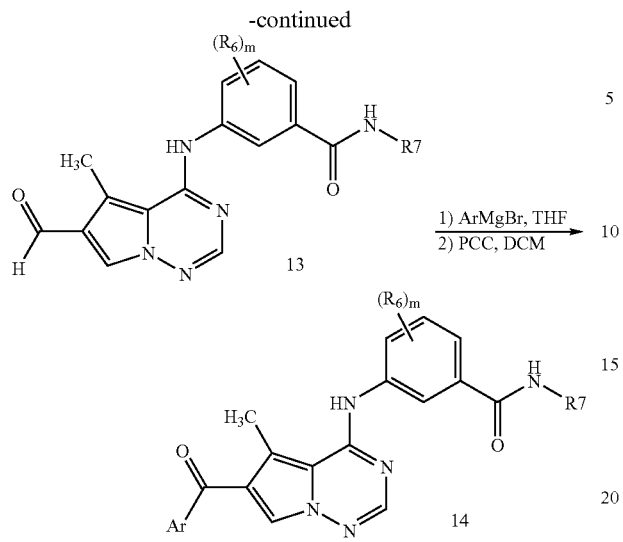

Reduction of the ester group of compound (5) (see Scheme 1), with a suitable reducing agent such as DIBAL-H in an aprotic organic solvent such as THF produces the alcohol (11). Alcohol (11) can be reacted with an amine RNH$_2$ in the presence of a coupling reagent, such as BOP, in an organic solvent, such as DMF, to afford the product (12). Product (12) is oxidized to aldehyde (13) with a suitable oxidant, such as MnO$_2$, in an organic solvent such as THF. Aldehyde (13) is reacted with a suitable organometallic reagent (such as phenylmagnesium bromide) to afford an intermediate secondary alcohol product that is subsequently oxidized to the ketone (14) with a suitable oxidant, such as PCC.

In addition, other compounds of formula I may be prepared using procedures generally known to those skilled in the art. In particular, the following examples provide additional methods for the preparation of the compounds of this invention.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

EXAMPLE 1

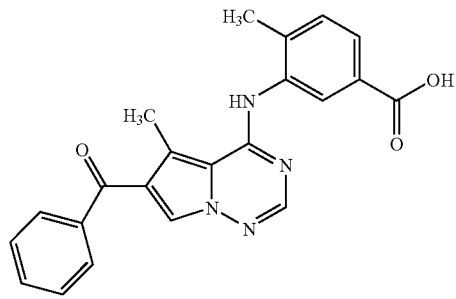

-continued

Step A:

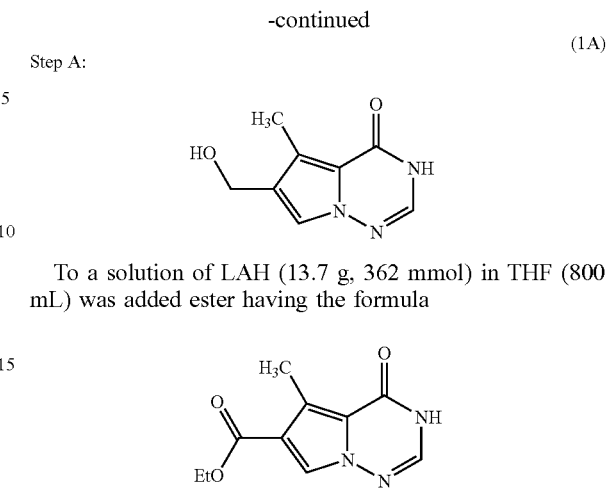

(1A)

To a solution of LAH (13.7 g, 362 mmol) in THF (800 mL) was added ester having the formula (8 g, 36.2 mmol) in several portions at rt. The reaction mixture was heated to reflux for 30 min., then cooled to rt, carefully quenched by being poured into ice water (1 L), and stirred rapidly for 1 h. The mixture was extracted with EtOAc and the combined extracts were washed with brine, dried over MgSO$_4$, filtered, and concentrated to give compound 1A (5.60 g, 86%).

Step B:

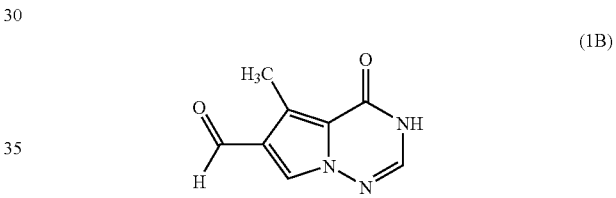

(1B)

To a suspension of compound 1A (1.0 g, 5.58 mmol) in acetone (80 mL) at 0° C. was added Jones Reagent (1.9 mL) dropwise. The reaction was stirred at 0° C. for 1 h, then carefully quenched with 2-propanol. Sat'd aq. sodium bicarbonate (100 mL) was added, and the mixture was extracted with EtOAc (5×100 mL). The combined extracts were washed with sat'd aq. sodium bicarbonate (1×100 mL), water (1×100 mL), and brine (1×100 mL), then dried over MgSO$_4$, filtered, and concentrated to afford compound 1B (647 mg, 65%). HPLC ret. t. (min): 1.50, MW: 177.16, LCMS[M+H]$^+$=178.

Step C:

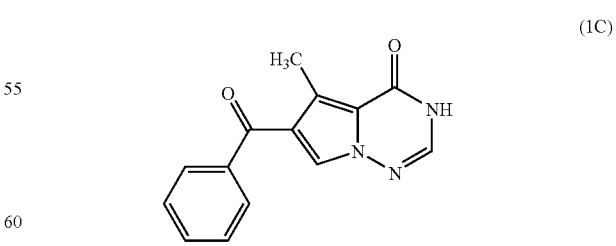

(1C)

To a solution of compound 1B (600 mg, 3.39 mmol) in THF (80 mL) at 0° C. was added phenylmagnesium bromide (3M, 2.94 mL, 8.8 mL) dropwise over 5 min. After stirring for 30 min at 0° C., the reaction was warmed to rt over 1 h and quenched with sat'd aq. ammonium chloride. The mixture was extracted with EtOAc and the extracts were dried, filtered, and concentrated to afford a benzylic alcohol intermediate. The crude benzylic alcohol intermediate was dissolved in acetone (50 mL) and cooled to 0° C. Jones Reagent (1 mL) was added dropwise and the reaction was stirred at 0° C. for 1 h, then carefully quenched with 2-propanol. Sat'd aq. sodium bicarbonate (50 mL) was added and the mixture was extracted with EtOAc (4×50 mL). The combined extracts were washed with sat'd aq. sodium bicarbonate (1×50 mL), water (1×50 mL), and brine (1×50 mL) before being dried over MgSO$_4$, filtered, and concentrated to afford compound 1C (563 mg, 66% over 2 steps). HPLC r.t. (min): 2.82 MW: 253.26 LCMS[M+H]$^+$=254.

Step D:

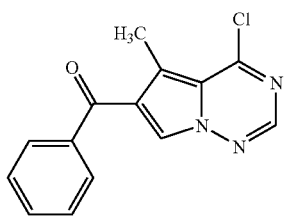

(1D)

Ketone 1C (152 mg, 0.6 mmol) was placed in POCl$_3$ (5 mL) and heated to 100° C. for 1.75 h. The reaction was cooled to rt and the excess POCl$_3$ was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over MgSO$_4$, filtered, and concentrated to afford the chloride 1D (163 mg, 100%).

Step E:

To a solution of chloride 1D (60 mg, 0.221 mmol) in DMF (1 mL) was added 3-amino-4-methyl-benzoic acid (66.8 mg, 0.442 mmol) and the solution was heated to 60° C. for 3 h. Water (5 mL) was added to precipitate the product, which was collected by filtration, washed with water, and allowed to air dry to give Example 1 (75 mg, 88%) HPLC ret. t. (min): 3.38, MW: 386.41, LCMS[M+H]$^+$=387.

EXAMPLES 2-3

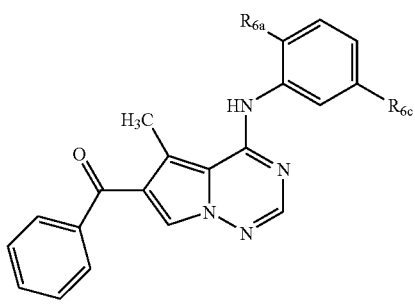

(Ic)

Compounds having the formula (Ic), wherein R$_{6a}$ and R$_{6c}$ have the values listed in Table 1, were prepared following the same or similar method described above for Example 1, using a different amine in the last step in place of 3-amino-4-methyl-benzoic acid.

TABLE 1

| Ex. No. | R$_{6a}$ | R$_{6c}$ | MW | HPLC ret. t (min.) | MS (MH+) |
|---|---|---|---|---|---|
| 2 | Me | C(=O)NHMe | 399.46 | 3.18 | 400 |
| 3 | H | H | 328.38 | 3.20 | 329 |
| 4 | Me | NHCO$_2$Et | 429.48 | 3.70 | 430 |

EXAMPLE 5

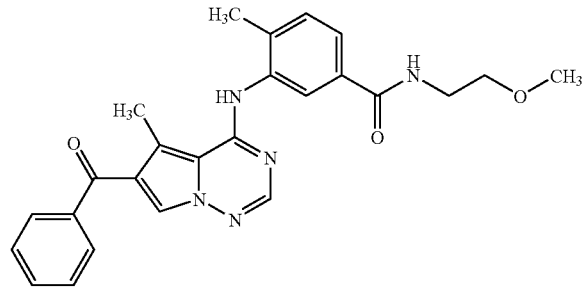

To a solution of Example 1 (30 mg, 0.078 mmol) and BOP (40 mg, 0.089 mmol) in DMF (0.5 mL) at room temperature was added 2-methoxyethylamine (0.017 mL, 0.194). The reaction was stirred at room temperature for 1 h and water (5 mL) was added to precipitate the product, which was collected by filtration, washed with water, and air dried to afford Example 5 (31 mg, 90%). HPLC ret.t. (min): 3.68, MW: 443.51, LCMS [M+H]$^+$=444.

EXAMPLES 6-10

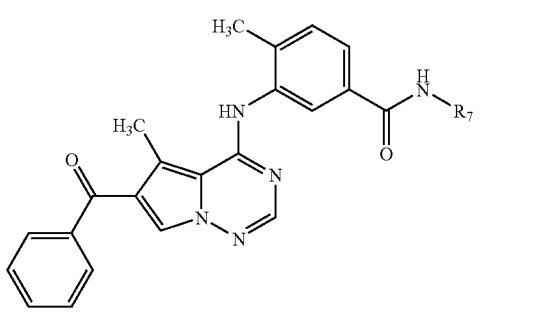

(Id)

Compounds having the formula (Id), wherein R$_7$ has the values listed in Table 2, were prepared following the same or similar method described above for Example 5, using a different amine in place of 2-methoxyethylamine.

TABLE 2

| Ex. No. | R$_7$ | MW | HPLC ret. t (min.) | MS (MH+) |
| --- | --- | --- | --- | --- |
| 6 | —CH$_2$CH$_2$OH | 429.48 | 3.14 | 430 |
| 7 | H | 385.43 | 3.28 | 386 |
| 8 | Et | 413.47 | 3.43 | 414 |
| 9 | Pr | 427.51 | 2.94 | 428 |
| 10 | Iso-Pr | 427.51 | 3.41 | 428 |

EXAMPLE 11

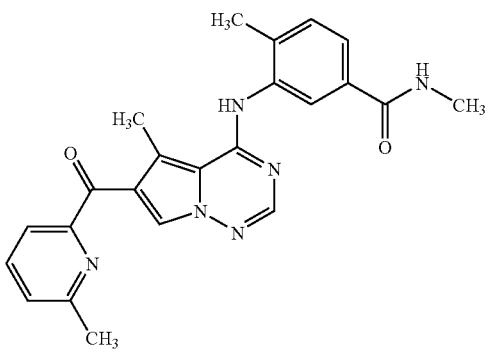

Step A:

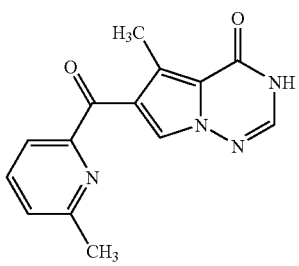

(11A)

To a solution of the compound 11B (160 mg, 0.90 mmol) in THF (10 mL) at 0° C. was added 6-methyl-2-pyridyl-magnesium bromide (0.25 M, 14.4 mL, 3.6 mL) dropwise over 5 min. After stirring for 30 min at 0° C., the reaction was warmed to rt and stirred for 16 h. Additional aliquots of 6-methyl-2-pyridylmagnesium bromide were added to complete the conversion of the starting material and the reaction was quenched with sat'd aq. ammonium chloride. The mixture was extracted with EtOAc and the extracts were dried, filtered, and concentrated to afford a reddish brown semi-solid material. This material was dissolved in acetone (10 mL) and cooled to 0° C. Jones Reagent (0.4 mL) was added dropwise and the reaction was stirred at 0° C. for 1 h, then carefully quenched with 2-propanol. Sat'd aq. sodium bicarbonate (15 mL) was added and the mixture was extracted with EtOAc (4×20 mL). The combined extracts were washed with sat'd aq. sodium bicarbonate (1×20 mL), water (1×20 mL), and brine (1×20 mL), then dried over MgSO$_4$, filtered, and concentrated to afford compound 11A (145 mg, 60% over 2 steps).

Step B:

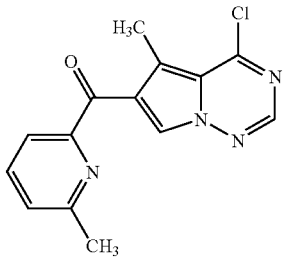

(11B)

Ketone 11A (75 mg, 0.28 mmol) was placed in POCl$_3$ (4 mL) and heated to 100° C. overnight. The reaction was cooled to rt and the excess POCl$_3$ was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over MgSO$_4$, filtered, and concentrated to afford the chloride 11B (64 mg, 79%).

Step C: Example 11

To a solution of compound 11B (11 mg, 0.038 mmol) in DMF (0.5 mL) was added N-methyl-3-amino-4-methyl-benzamide hydrochloride (17 mg, 0.084 mmol) and DIPEA (0.013 mL, 0.077 mmol) and the solution was heated to 60° C. for 2 h. Water (5 mL) was added to precipitate the product, which was collected by filtration, washed with water, and allowed to air dry to afford Example 11 (7.2 mg, 45%). HPLC ret. t. (min):2.80, MW: 414.47, LCMS[M+H]$^+$=415.

EXAMPLE 12

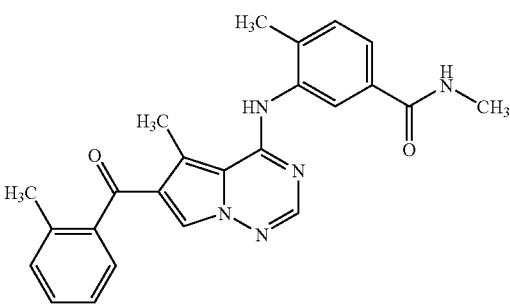

Step A:

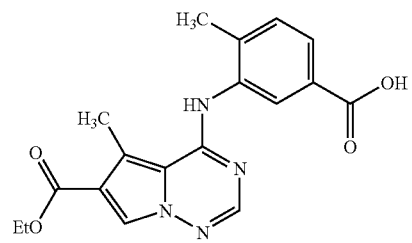

(12A)

To a solution of the chloride having the formula

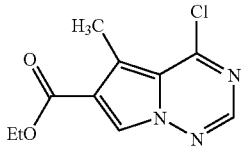

(10 g, 41.8 mmol) in DMF (60 mL) was added 3-amino-4-methyl-benzoic acid (6.3 g, 41.8 mmol) at rt. The reaction mixture was stirred for 16 h, poured into water (500 mL) and stirred rapidly for 1 h. The solids were filtered, washed with water (500 mL), and air dried to give the compound 12A (13.6 g, 92%) as a light pink solid. MS[M+H]$^+$=355.

Step B:

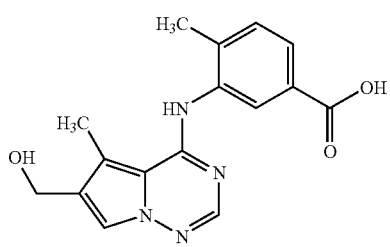

To a solution of the compound 12A (1 g, 2.8 mmol) in DCM (6 mL) at −78° C. was added DIBAL-H (1M, 8.5 mL, 8.5 mmol) dropwise. The reaction was stirred for 2 h at −78° C., warmed to rt over 1.5 h, quenched with sat'd aq. NH$_4$Cl, then HCl (1 N) was added to adjust the pH to 4 and the solution was extracted with EtOAc. After drying of the organic phases and concentration, compound 12B was obtained as a pink solid (874 mg, 100%). HPLC ret. t. (min): 1.74, MW: 312.33, and LCMS[M+H]$^+$=313.

Step C:

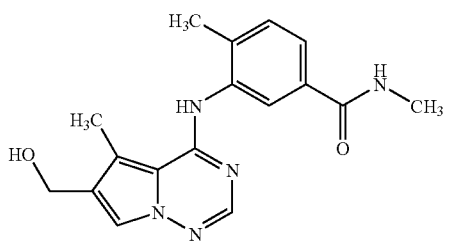

To a solution of compound 12B (1 g, 3.2 mmol) in DMF (10 mL) was added BOP (1.5 g, 3.5 mmol), methylamine hydrochloride (1.07 g, 16 mmol), and triethylamine (2.3 mL, 16 mmol). The reaction was stirred overnight at room temperature, then poured into water (60 mL) to precipitate the product. The solids were collected by filtration and allowed to air dry to give compound 12C (1.1 g, 100%). HPLC ret. t. (min): 1.43, MW: 325.37, LCMS[M+H]$^+$=326.

Step D:

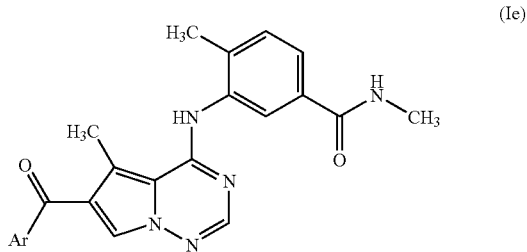

To a solution of compound 12C (25 mg, 0.08 mmol) in THF (1.5 mL) at room temperature was added MnO$_2$ (104.4 mg, 1.2 mmol). After stirring 40 min, the reaction was completed. The product was collected by filtration and the precipitate was washed with acetonitrile. After drying of the filtrate and concentration, aldehyde 12D was obtained as a yellow oil (22 mg). HPLC ret. t. (min): 2.28, MW: 323.36, LCMS[M+H]$^+$=324.

Step E: Example 12

To a solution of compound 12D (50 mg, 0.16 mmol) in THF (2 mL) at 0° C. was added 2-methyl-phenylmagnesium bromide (2 M, 0.280 mL, 0.56 mmol) dropwise. The reaction was stirred at 0° C. for 30 min, then the temperature was raised to room temperature. After stirring for 2 h, the reaction was quenched with saturated aq. NH$_4$Cl (2 ml). The desired product was extracted with ethyl acetate and dried to afford an intermediate alcohol as a yellow solid (78.7 mg, crude, quant.) LCMS [M+H]$^+$=416. To a solution of the crude alcohol (66 mg, 0.16 mmol) in DCE (5 mL) at room temperature was added pyridinium chlorochromate (86 mg, 0.4 mmol). After stirring 1 h, the reaction was quenched with water (2 mL). The desired product was extracted with ethyl acetate and dried (87.7 mg). After purification with preparative HPLC, Example 12 was obtained as yellow solid (6.2 mg, 10%). HPLC ret. t. (min): 3.33, MW: 413.48, LCMS [M+H]$^+$=414.

EXAMPLES 13-17

Compounds having the formula (Ie), wherein Ar has the values listed in Table 3, were prepared following the same or similar method described above for Example 12, using a different phenylmagnesium bromide in the last step.

TABLE 3

| Ex. No. | Ar | MW | HPLC ret. t. (min.) | MS (MH+) |
|---|---|---|---|---|
| 13 | 4-F-phenyl | 417.45 | 3.27 | 418 |
| 14 | 3-OMe-phenyl | 429.48 | 3.29 | 430 |
| 15 | 2-OMe-phenyl | 429.48 | 2.98 | 430 |
| 16 | 3-F-phenyl | 417.45 | 2.98 | 418 |
| 17 | benzo[1,3]dioxole | 443.47 | 3.30 | 444 |

What is claimed is:

1. A compound of formula (Ib)

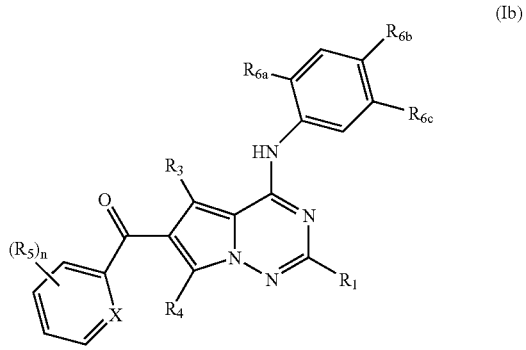

(Ib)

or a pharmaceutically-acceptable salt thereof, wherein:
X is N or CH;
$R_1$ and $R_4$ are each hydrogen;
$R_3$ is methyl;
$R_5$ is attached to any available carbon atom of the aryl or heteroaryl ring and at each occurrence is independently selected from methyl, fluoro and —$OCH_3$, and/or two of the $R_5$ groups may be taken together to form

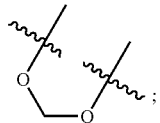

;

$R_{6a}$ is selected from hydrogen or methyl;
$R_{6b}$ is hydrogen;
$R_{6c}$ is selected from hydrogen, —COOH, —C(=O)$NH_2$, —C(=O)$NHCH_3$, —C(=O)$NHCH_2CH_3$, —C(=O)$NHR_7$, where $R_7$ is alkoxy, —C(=O)NH($CH_2$)$_2OCH_3$, —C(=O)NH($CH_2$)$_2$OH, —C(=O)NH($CH_2$)$_2CH_3$, —C(=O)$NHCH_2(CH_2)CH_3$, and —$NHCO_2CH_2CH_3$; and —$NHCO_2CH_2CH_3$; and
n is 0, 1 or 2.

2. A pharmaceutical composition comprising one or more compounds according to claim 1 and a pharmaceutically-acceptable carrier or diluent.

3. A method of treating asthma, adult respiratory distress syndrome, chronic obstructive pulmonary disease, chronic pulmonary inflammatory disease, inflammatory bowel disease, osteoporosis, psoriasis, graft vs. host rejection, atherosclerosis, multiple myeloma, myocardial ischemia, rheumatoid arthritis, psoriatic arthritis, traumatic arthritis, rubella arthritis, gouty arthritis and osteoarthritis, comprising administering to a patient in need of such treatment a pharmaceutical composition according to claim 2.

* * * * *

UNITED STATES PATENT AND TRADEMARK OFFICE
CERTIFICATE OF CORRECTION

PATENT NO. : 7,314,876 B2 Page 1 of 1
APPLICATION NO. : 10/420445
DATED : January 1, 2008
INVENTOR(S) : Dyckman et al.

It is certified that error appears in the above-identified patent and that said Letters Patent is hereby corrected as shown below:

Claim 1, column 28, line 41, delete "and $NHCO_2CH_2CH_3$; and".

Signed and Sealed this

Seventeenth Day of June, 2008

JON W. DUDAS
*Director of the United States Patent and Trademark Office*